CHRYSANTHEMUM PLANT
Filed Dec. 10, 1971
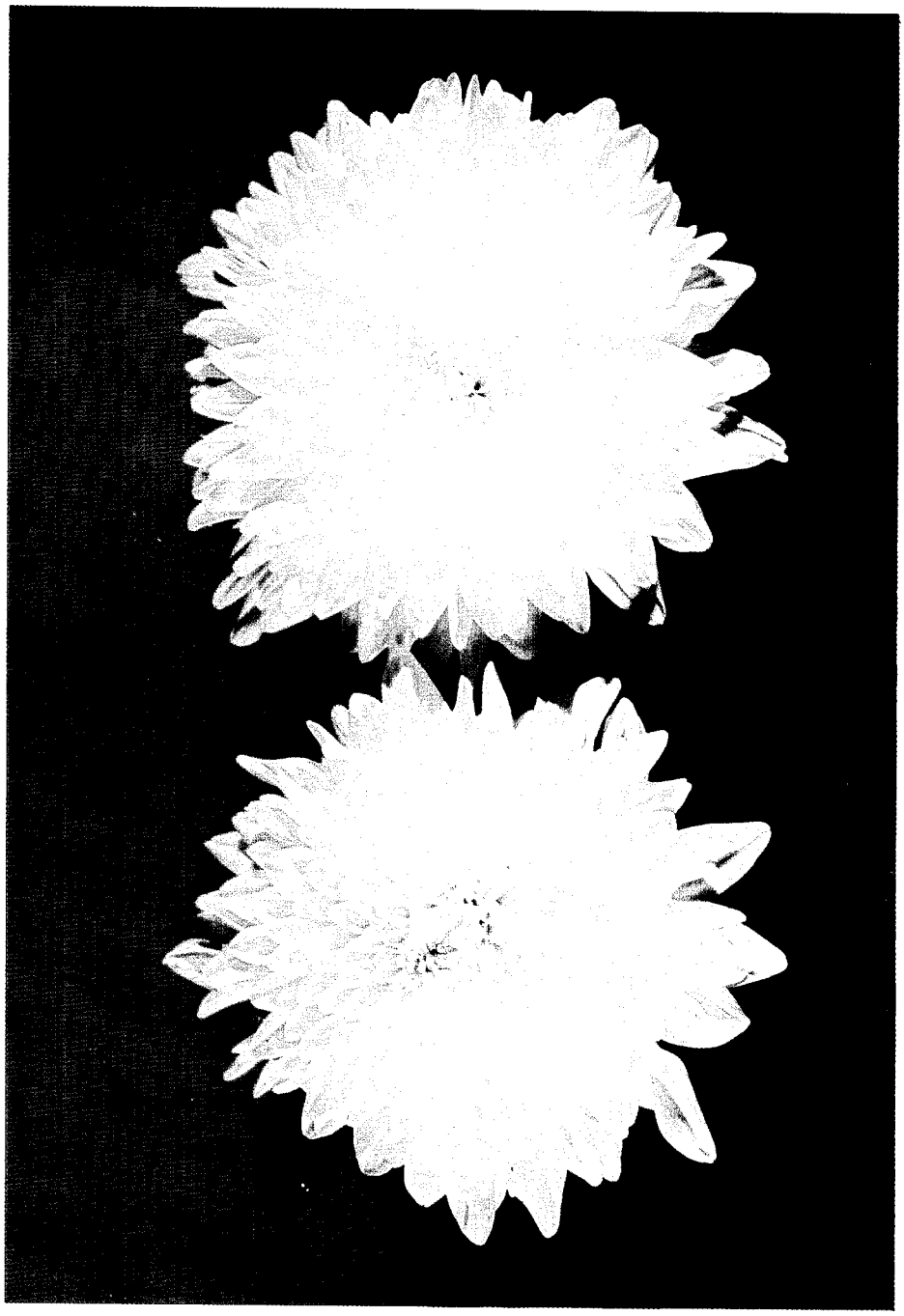

CHRYSANTHEMUM PLANT
Filed Dec. 10, 1971
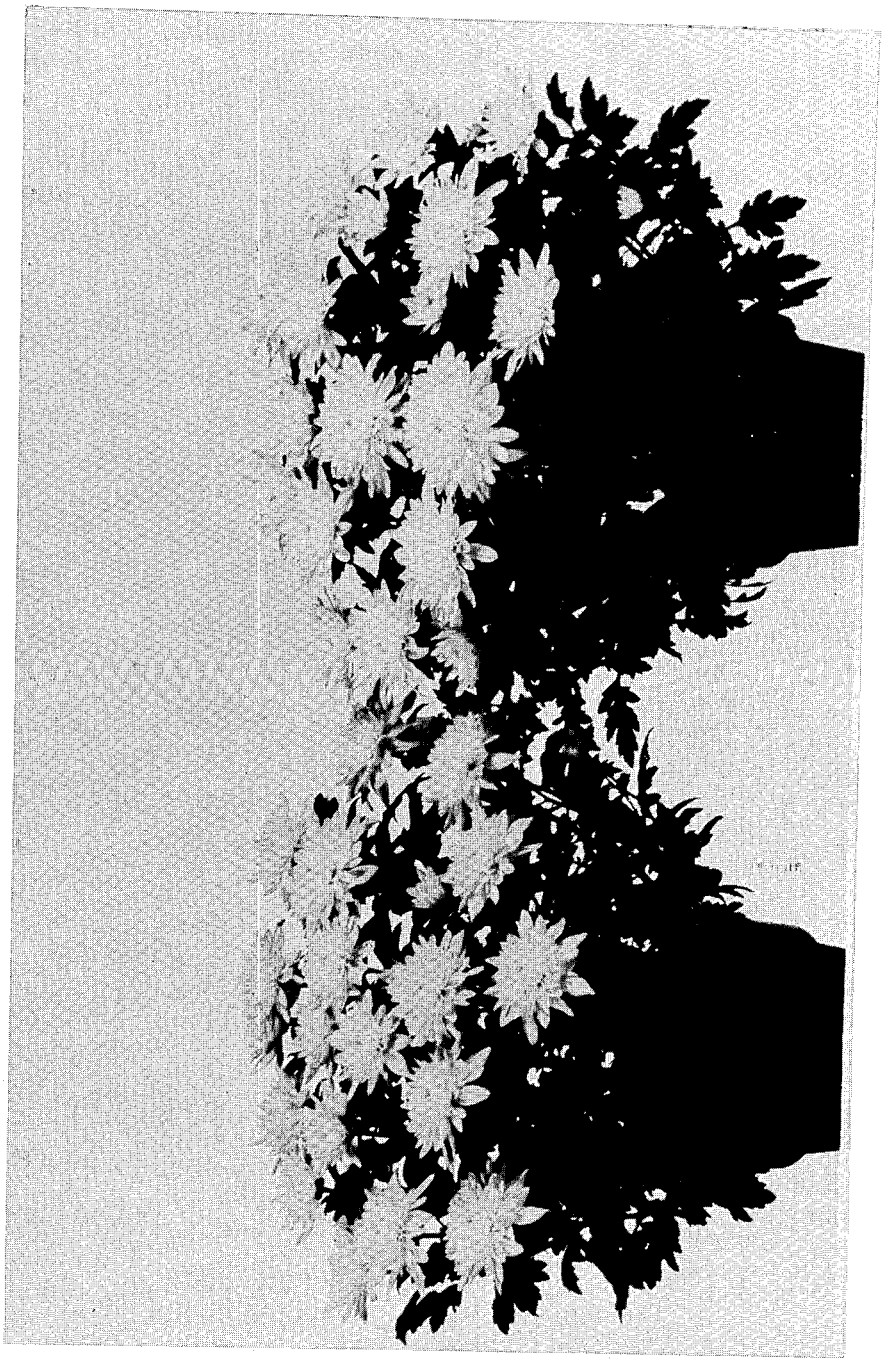

United States Patent Office

Plant Pat. 3,424
Patented Jan. 8, 1974

3,424
CHRYSANTHEMUM PLANT

Walter H. Jessel, Jr., Doylestown, and William E. Duffett, Akron, Ohio, assignors to Yoder Brothers, Inc., Barberton, Ohio

Filed Dec. 10, 1971, Ser. No. 206,954
Int. Cl. A01h *5/00*
U.S. Cl. Plt.—78 1 Claim

The present invention comprises a new and distinct cultivar of chrysanthemum plant which is a sport of the unpatented cultivar known in the United States as Puritan.

The new cultivar is similar in many respects to Puritan, having the same characteristics of:

(1) Decorative flower form.

(2) Recommended year-round flowering period.

The new cultivar is distinguished from Puritan by the following characteristics when grown under comparable conditions:

(1) Its yellow color.

(2) The flower is approximately one-quarter inch smaller in diameter.

(3) Approximately one to two inches shorter habit.

(4) Approximately two to five days later response. The response difference is greatest during low light periods of winter, and is least during high light, high temperature periods because the response of the parent Puritan slows to a greater extent in high temperatures than Yellow Puritan itself.

(5) Slightly lighter foliage color.

The new cultivar was selected from a flowering block of the parent cultivar at Barberton, Ohio, and when asexually reproduced by cuttings at Barberton, Ohio, has been found to retain its distinctive characteristics through successive propagations.

The new cultivar when grown in the vicinity of Barberton, Ohio, has a response period of approximately 9–10 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from January through December; in coastal California, January through December; and Florida, November through mid-May.

The accompanying drawings shows the unique characteristics of the new cultivar. Sheet 1 comprises a color comparison photograph, with the new cultivar appearing on the left and the parent cultivar Puritan on the right. Sheet 2 comprises a black and white comparison photograph, intended to show the somewhat later response and shorter habit of the new cultivar, with the new cultivar appearing on the left and the cultivar Puritan on the right.

In the description which follows, color references are made to the Munsell Color Book, 1963 edition, and comparisons are made with the cultivar Puritan. Where only a single value or description appears for the new cultivar, the same value or description applies as well to the parent cultivar Puritan.

Botanical classification: *Chrysanthemum morifolium*

| | Yellow Puritan | Puritan |
|---|---|---|
| Bloom: | | |
| Size | 3¾″. | 4″. |
| Fully expanded | 4¾″. | 5″. |
| Borne | Singly, on disbudded branches | |
| Stems | Strong | |
| Form | Decorative | |
| Permanence | 10–12 days | |
| Color (Munsell): | | |
| Center of flower | Yellow, 6.25Y8.5/12 | Light yellow-green, 1.5GY9/4. |
| Base of petals | Yellow-green, 2.5GY8/8 | Yellow-green, 2.5GY7/10. |
| Inside of petals | Yellow, 6.25Y8.5/12 to light yellow, 7.5Y8.5/8 | White, N9.5/. |
| Reverse of petals | do | Do. |
| Tonality from a distance | Yellow | White. |
| Discoloration | Light yellow, 7.5Y8.5/8 | White N9.5/. |
| Petals: | | |
| Texture | Smooth | |
| Appearance and form | Closed to tubular at base, deep furrowed keel, tapering to a blunt tip. | |
| Arrangement | Composite, whorled on a single receptacle | |
| Persistence | Resist shatter | |
| Fragrance | Typical chrysanthemum | |
| Reproductive organs: | | |
| Stamen, anthers | 0–5 | |
| Pollen | None to very scant | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Semi-upright | |
| Height | Approximately 10″ to 11″ when given 9–10 week medium treatment as defined for the various seasons in the timetables of Yoder Brothers, Inc., Barberton, Ohio. | Approximately 12″ when given 9 week medium treatment as defined for the various seasons in the timetables of Yoder Brothers, Inc., Barberton, Ohio. |
| Spread | Approximately 5½″ when given 9–10 week medium treatment as defined for the various seasons in the timetables of Yoder Brothers, Inc., Barberton, Ohio. | Approximately 6″ when given 9 week medium treatment as defined for the various seasons in the Yoder timetables. |
| Foliage: | | |
| Top side | Green, 7.5GY3/4 | Dark green, 7.5GY2/4. |
| Size | 3½″ long, 2″ wide | 3¾″ long, 2″ wide. |
| Quantity | Numerous | |
| Shape | Spatulate lobed | |
| Texture | Coarse | |
| Ribs and veins | Prominent | |
| Edge | Moderately indented | |
| Serration | Coarse | |
| Underside | Light green, 7.5GY5/4 | Medium green, 7.5GY4/4. |
| Stipules | Prominent | |

We claim:

1. A new and distinct cultivar of chrysanthemum characterized particularly as to its uniqueness when compared to the parent cultivar Puritan by its yellow flower color; approximately one-quarter inch smaller diameter flowers; approximately one to two inches shorter plant habit; its slightly lighter foliage color and its approximately two to five days later response, with such response difference being greatest during low light periods of winter, and least during high light, high temperature periods.

No references cited.

ROBERT E. BAGWILL, Primary Examiner